United States Patent [19]

Louise et al.

[11] Patent Number: 5,316,481

[45] Date of Patent: May 31, 1994

[54] SYSTEM FOR DISPLAYING AND SELECTING HAIR DYE SHADES

[75] Inventors: John Louise, New York, N.Y.; Thomas Rushing, Denville, N.J.

[73] Assignee: Clairol, Inc., New York, N.Y.

[21] Appl. No.: 16,397

[22] Filed: Feb. 11, 1993

[51] Int. Cl.⁵ .................................................. G09B 19/00
[52] U.S. Cl. .......................................... 434/99; 434/98
[58] Field of Search ................... 434/98, 99; 132/212; 40/584

[56] References Cited

U.S. PATENT DOCUMENTS

| | | | |
|---|---|---|---|
| D. 276,661 | 12/1984 | Cafazzo | 434/99 X |
| 2,221,774 | 11/1940 | Bowser | 434/99 |
| 3,000,113 | 9/1961 | Olson | 434/98 |
| 3,609,886 | 10/1971 | Vien | 434/99 |
| 3,702,508 | 11/1972 | Netter | 434/99 |

Primary Examiner—Gene Mancene
Assistant Examiner—Cindy A. Cherichetti
Attorney, Agent, or Firm—Anthony M. Santini; Doreen F. Shulman

[57] ABSTRACT

A system for displaying and selecting, a process for selecting, and a device for selecting hair dye shades, which allow the consumer to make a knowledgeable and informed hair dye selection. A horizontal or vertical axis along which hair dyes are arranged by similar colors and shades; another axis, perpendicular to the first axis, along which hair dyes are arranged by the length of duration of effect; a hair dye shade selector comprising color samples that each represent the haircolor that will result when hair of a particular color is treated with a particular hair dye are included; on-shelf consumer education and instruction materials regarding hair dye; display system indicators; and packaging indicators.

16 Claims, No Drawings

SYSTEM FOR DISPLAYING AND SELECTING HAIR DYE SHADES

BACKGROUND OF THE INVENTION

This invention relates to a system for displaying and selecting, a process for selecting, and a device for selecting hair dye shades, which allow consumers to make a knowledgeable and informed hair dye selection.

People who are interested in coloring their hair often do not do so because they have no way of knowing what color their hair will be after they apply a particular dye treatment. This occurs because the haircolor shown on the package of hair dye (usually a portrait of a model) typically represents the haircolor that would result when virgin white hair is treated with the hair dye in that package. Even when swatches of dyed hair are displayed on the retail shelf next to a corresponding hair dye, the consumer cannot be confident that their haircolor, after the dye treatment, will match the swatch color. Such swatches usually also only represent the haircolor that would result by treating virgin white hair with the dye. Thus, the consumer is left to guess what color their hair will be after dye treatment.

Confusion about the varying duration of the effect of different hair dyes also deters potential hair dye consumers. Many consumers don't fully understand the difference between, for example, permanent, demi-permanent and semi-permanent hair dye. Consumers are also confused about the different types of hair dyes. Many consumers don't fully understand the difference between, for example, gray coverage, color enhancement and highlights.

In the past, some attempts have been made to alleviate the confusion and lack of information that besets consumers who are selecting a hair dye. One such attempt involved only organizing the hair dye packaging display with similar hair dye shades grouped together either horizontally or vertically and with different durations/types of hair dye shades grouped together in the opposite perpendicular direction. Another such attempt only involved artificial hair swatches representing three natural haircolor shades that had each been separately treated with one of several hair dye shades. However, these attempts, by themselves, did not alleviate the consumers' confusion and lack of information regarding hair dye selection.

Therefore there exists a need in the art for a coordinated system for displaying and selecting, a process for selecting, and a device for selecting hair dye shades, which allows the consumer to make a confident and informed hair dye selection.

SUMMARY OF THE INVENTION

It is an object of this invention to provide a coordinated system for displaying and selecting hair dye shades that allows the consumer to know the haircolor that will result when their hair is treated with a particular dye shade.

It is also an object of this invention to provide a coordinated system for displaying and selecting hair dye shades that informs the consumer about the duration of the effect of different hair dyes.

It is also an object of this invention to provide a coordinated system for displaying and selecting hair dye shades that informs the consumer about the differences between different types of hair dyes.

It is further an object of this invention to provide a process for selecting hair dye shades that allows the consumer to know the haircolor that will result when their hair is dyed with a particular dye shade.

It is also an object of this invention to provide a device for selecting hair dye shades that allows the consumer to know the haircolor that will result when their hair is dyed with a particular dye shade.

In accordance with this invention, a system for displaying and selecting, a process for selecting, and a device for selecting hair dye shades, which allows the consumer to make a knowledgeable and informed hair dye selection, are provided.

DETAILED DESCRIPTION OF THE INVENTION

The coordinated hair dye selection and display system of this invention comprises a horizontal or vertical first axis along which hair dyes are arranged by similar colors and shades; a second axis, perpendicular to the first axis, along which hair dyes are arranged by the duration of their effect; a hair dye shade selector comprising color samples that each represent the haircolor that will result when hair of a particular original color is treated with a particular hair dye shade; on-shelf consumer education and instruction materials regarding hair dye; display system indicators; and packaging indicators.

The duration axis is divided into several commitment levels that relate to the duration of the effect of the hair dye. For example, level one corresponds to a low commitment level and all of the semi-permanent hair dyes are displayed adjacent to level one. Semi-permanent hair dyes last for 6 to 12 shampoos. Level two corresponds to a medium commitment level and all of the demi-permanent hair dyes are displayed adjacent to level two. Demi-permanent hair dyes last for 12 to 24 shampoos. Level three corresponds to a high commitment level and all of the permanent hair dyes are displayed adjacent to level three. Permanent hair dyes are not generally removed by shampooing. Hair treated with permanent hair dye grows out as new hair grows in.

Preferably, duration level indicators and explanations are displayed on the hair dye display and selection system of this invention. Optionally, indicators on the hair dye packaging may reiterate the appropriate duration level, with or without its explanation. These display and packaging indicators coordinate the elements of the hair dye display and selection system of this invention.

The color axis is divided into several sections that relate to the general color the consumer would like his or her hair to be after it is dyed. These general color sections may be blonde, red, brown and black. All of the hair dyes that produce a particular general color are displayed in the appropriate general color section. Preferably, general color section indicators are displayed on the hair dye display and selection system of this invention. In addition, individual hair dye packages will indicate the haircolor shade of the dye in the package. These display and packaging indicators coordinate the elements of the hair dye display and selection system of this invention.

The hair dye shade selector comprises color samples that each represent the haircolor that will result when hair of a particular original color is treated with a particular hair dye. The color samples are created by dividing natural haircolors into several categories. These categories could be, for example, light/medium blonde, dark blonde, light brown, medium brown, dark brown, and black. Hair swatches representing each of these categories are then separately dyed with one of from several to all shades of from several to all types of hair dye that will be displayed on the retail shelf corresponding to the hair dye shade selector.

The resulting haircolor color samples may be displayed in many ways. For example, the color sample may be a card with one haircolor or a strip of several haircolors. The haircolors represented on the color samples may be in the form of colored shapes, similar to what is traditionally used to select interior or exterior house paint. Preferably, the haircolors represented on the color samples are in the form of artificial hair swatches.

This innovative hair dye shade selector allows the consumer, for example, to see that when blonde hair is treated with a specific semi-permanent red hair dye shade, the result will look very different than when brown hair is treated with that same semi-permanent red hair dye shade. It also allows the consumer, for example, to see that when brown hair with some gray is treated with a specific semi-permanent blonde hair dye shade, the result will look very different than when that same brown hair is treated with a specific permanent blonde hair dye of a similar shade.

The coordinated hair dye selection and display system of this invention may also have on-shelf consumer education and instruction materials relating to hair dye. Such materials may include a computer that will prompt the consumer through several stages of the hair dye selection process. Such materials may also include flip charts, brochures, and the like, which explain various aspects of the coordinated hair dye selection and display system of this invention. These educational materials also coordinate the elements of the hair dye display and selection system of this invention.

Together, the horizontal or vertical axis along which hair dyes are arranged by similar colors and shades; the other axis, perpendicular to the first axis, along which hair dyes are arranged by the length of duration of their effect; the hair dye shade selector comprising color samples that each represent the haircolor that will result when hair of a particular original color is treated with a particular hair dye shade; the on-shelf consumer education and instruction materials regarding hair dye; the display system indicators; and packaging indicators comprise a coordinated hair dye selection and display system. This system allows consumers to make a confident and informed hair selection. The consumer no longer has to guess what color their hair will be after dye treatment or how long the effect of the hair dye will last.

The hair dye selection and display system of this invention may also have a section of products that produce special effects on the hair. Such special effects include highlighting, frosting and miscellaneous haircolor products. Optionally, special effects section indicators are displayed on the hair dye display and selection system of this invention.

The hair dye selection and display system of this invention may be free-standing or the elements of the system may be adapted to existing retail shelf space.

The process of this invention for selecting a hair dye shade comprises using the hair dye shade selector described above.

One specific example of how the hair dye selection and display system of this invention works is as follows. A consumer approaches the hair dye selection and display system of this invention. The consumer has light brown hair but would like to have dark brown hair. The consumer's eyes move horizontally to the brown general color section. When the consumer looks vertically up and down from that horizontal position, the consumer sees several types of brown hair dye. By reading a duration level indicator or explanation on the display and selection system or the hair dye package, the consumer selects the duration or commitment level that is appropriate for his or her needs. The consumer's eyes then move vertically to the appropriate duration level section that is within the selected general color section. The consumer now has to choose from several haircolor shades within the desired general color section and duration level. For assistance in selecting a shade of hair dye, the consumer uses the hair dye shade selector of this invention. The consumer, who has light brown hair, goes to the section of the shade selector that holds color samples of light brown hair that have each been treated with one of the several haircolor shades within the desired general color section and duration level. The consumer selects the most desirable shade and takes the corresponding package of hair dye from the shelf.

It will be apparent to those skilled in the art that the invention described herein can be practiced by other that the embodiments disclosed herein, which are presented for the purpose of illustration and not of limitation, and the present invention is limited only by the claims that follow.

We claim:

1. A hair dye selection and display shelf system comprising:
   (a) a first plurality of hair dye products arranged by dye color shade graduation along a first axis of a display shelf wherein the lightest dye color shade is at one end of said display shelf along said first axis and the darkest dye color shade is at a distal end;
   (b) a second plurality of hair dye products arranged by duration of hair dye effect along a second axis of said display shelf perpendicular to said first axis, wherein the shortest duration of hair dye effect is at one end of said display shelf along said second axis and the longest duration of effect is at a distal end;
   (c) indicia for distinguishing between said dye color shades and said dye durations is provided on at least one of said display shelf and said hair dye products; and
   (d) hair dye shade selection means connected to said display shelf comprising a plurality of natural hair color shades and a plurality of resulting hair dye color shades for identifying a resulting hair dye color shade when a selected natural hair color shade is treated with a hair dye product of selected dye color shade and selected duration of effect.

2. The system of claim 1 further comprising digitized instructional means connected to said display shelf for directing a user through a hair dye selection process.

3. The system of claim 1, wherein the color shade graduations consist essentially of blond, red, brown and black.

4. The system of claim 3, wherein the resulting color shade graduations are arranged along said first axis in a sequential order of blond, followed by red, followed by brown, and followed by black.

5. The system of claim 1, wherein the hair dye durations consist essentially of semi-permanent hair dyes, demi-permanent hair dyes and permanent hair dyes.

6. The system of claim 5, wherein the hair dye durations are arranged along said second axis in a sequential order of semi-permanent hair dyes, followed by demi-permanent hair dyes, and followed by permanent hair dyes.

7. The system of claim 1, wherein the natural hair color shade is selected from the group consisting of light/medium blond, dark blond, light brown, medium brown, dark brown and black.

8. The system of claim 1 comprising a self-supporting, free-standing article.

9. The system of claim 1 adapted to be incorporated into an existing retail shelf space.

10. A process for selecting and displaying a hair dye product on a shelf system comprising:
   (a) arranging a first plurality of hair dye products by dye color shade graduation along a first axis of a display shelf;
   (b) further arranging said first plurality of hair dye products with the lightest color at one end of said display shelf along said first axis and the darkest color at a distal end;
   (c) arranging a second plurality of hair dye products by duration of hair dye effect along a second axis of said display shelf perpendicular to said first axis;
   (d) further arranging said second plurality of hair dye products with the products of shortest duration at one end of said display shelf along said second axis and the products of the longest duration at a distal end;
   (e) providing indicia on at least one of said display shelf and said hair dye products for distinguishing between the dye color shades and dye durations;
   (f) providing hair dye shade selection means, and connecting said selection means to said display shelf, to identify a resulting hair dye color shade when a selected natural hair color shade is treated with a hair dye product of selected dye color shade and selected duration of effect; and
   (g) providing digitized instructional means, and connecting said instructional means to said display shelf, to direct a user through a hair dye selection process.

11. The process of claim 10, wherein the color shade graduations consist essentially of blond, red, brown and black.

12. The process of claim 11, wherein the resulting color shade graduations are arranged along said first axis in a sequential order of blond, followed by red, followed by brown, and followed by black.

13. The process of claim 10, wherein the hair dye durations consist essentially of semi-permanent hair dyes, demi-permanent hair dyes and permanent hair dyes.

14. The process of claim 13, wherein the hair dye durations are arranged along said second axis in a sequential order of semi-permanent hair dyes, followed by demi-permanent hair dyes, and followed by permanent hair dyes.

15. The process of claim 10, wherein the natural hair color shade is selected from the group consisting of light/medium blond, dark blond, light brown, medium brown, dark brown and black.

16. The process of claim 10 carried out on an existing retail shelf space.

* * * * *